United States Patent [19]

Yamaguchi

[11] 4,057,391

[45] Nov. 8, 1977

[54] STEAM STERILIZATION OF MATERIALS IN SEALED PACKAGES

[75] Inventor: Kanemichi Yamaguchi, Yokohama, Japan

[73] Assignee: Toyo Seikan Kaisha Ltd., Japan

[21] Appl. No.: 646,027

[22] Filed: Jan. 2, 1976

Related U.S. Application Data

[63] Continuation of Ser. No. 469,690, May 13, 1974, abandoned.

[30] Foreign Application Priority Data

May 22, 1973 Japan .................... 48-57022
May 22, 1973 Japan .................... 48-57023

[51] Int. Cl.² ................... A61L 1/00; A61L 3/00; A23L 3/10
[52] U.S. Cl. ............................ 21/56; 21/94; 99/483; 426/401; 426/521
[58] Field of Search ............. 21/56, 94–99; 426/399, 401, 521; 99/483

[56] References Cited

U.S. PATENT DOCUMENTS

| 1,902,625 | 3/1933 | Dunham ........................ 21/94 |
| 2,082,460 | 6/1937 | Omsted ........................ 21/96 X |
| 2,539,505 | 1/1951 | Barnum et al. ................ 21/99 X |
| 3,086,837 | 4/1963 | Wilkinson et al. ............. 21/56 |
| 3,107,975 | 10/1963 | Linder ........................ 21/94 |
| 3,366,442 | 1/1968 | Neiss ........................ 21/94 X |
| 3,481,688 | 12/1969 | Craig et al. ................. 426/521 |
| 3,531,300 | 9/1970 | Greenberg et al. ............. 21/56 |
| 3,619,126 | 11/1971 | Carvallo ..................... 21/94 |
| 3,773,466 | 11/1973 | Linder ....................... 21/94 |
| 3,852,508 | 12/1974 | De Voe ....................... 426/521 |
| 3,897,818 | 8/1975 | Champel ...................... 21/94 X |

OTHER PUBLICATIONS

Darling, Charles S.; Exhaust Steam Engineering; Chapman & Hall; London; 1928 pp. 246–257.

Primary Examiner—Norman Yudkoff
Assistant Examiner—Barry I. Hollander
Attorney, Agent, or Firm—Wenderoth, Lind & Ponack

[57] ABSTRACT

In a method and apparatus for batch type sterilization of the type wherein sealed packages to be sterilized are charged into a sterilizing tank, steam is admitted into the tank, and then cooling water is admitted into the tank for cooling the sterilized packages, there is provided a heat storage tank which is heated by steam from an independent boiler for supplying steam to the sterilizing tank during the heating up step and subsequent sterilizing step which is effected at a constant temperature. During the cooling step, cooling water is admitted into the sterilizing tank from the top and bottom thereof and the cooling water in the lower portion is sprayed into the upper portion by means of a circulating pump.

5 Claims, 1 Drawing Figure

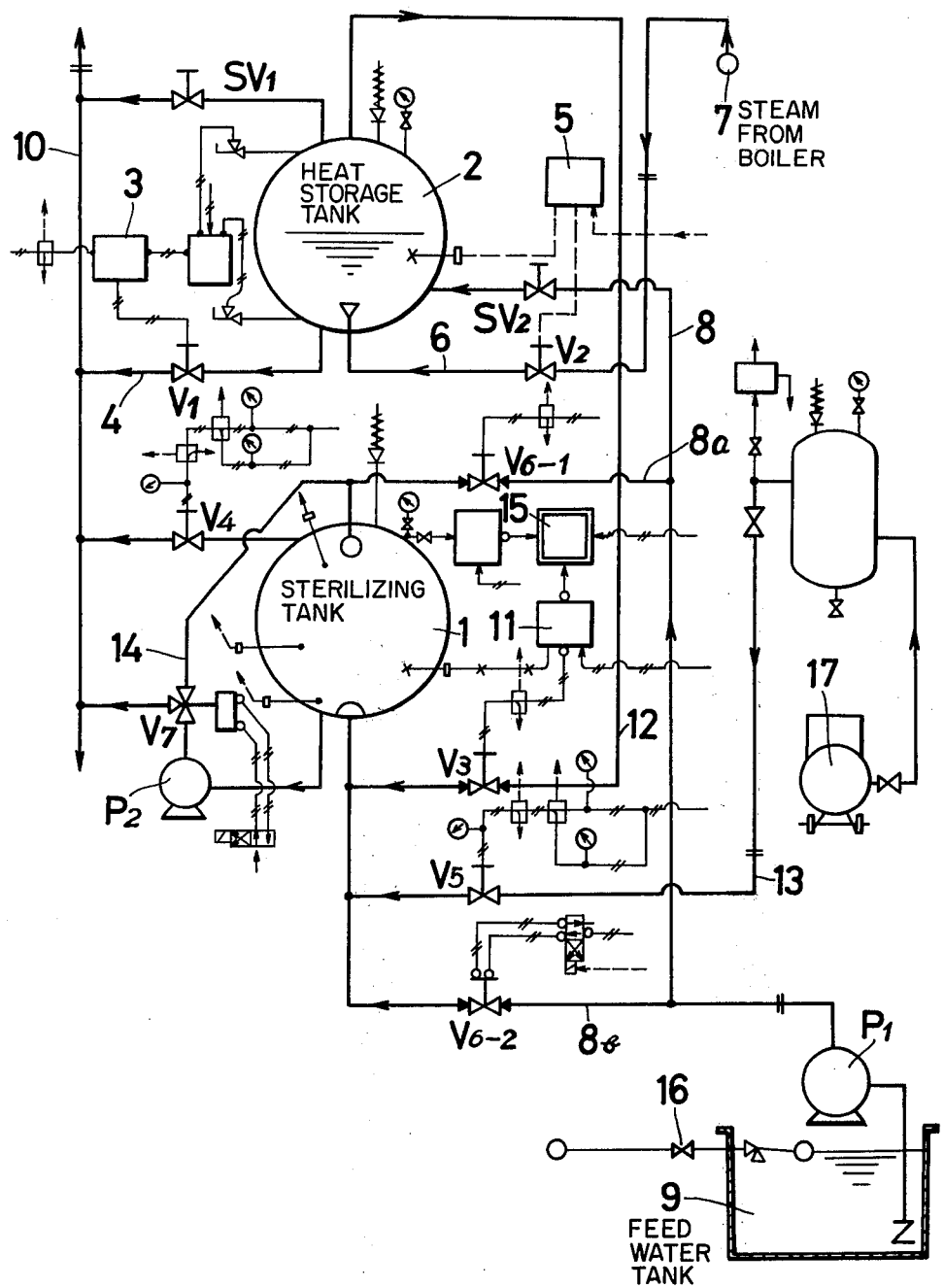

STEAM STERILIZATION OF MATERIALS IN SEALED PACKAGES

This is a continuation, of application Ser. No. 469,690, filed May 13, 1974, now abandoned.

BACKGROUND OF THE INVENTION

This invention relates to improvements in a method of batch type sterilization by heating which comprises packing a substance to be sterilized such as foodstuff in flexible containers the innermost layers of certain portions thereof being made of films having heat sealing property or in containers which are liable to be broken due to the pressure difference between inside and outside of the containers, charging such packages into a sterilizing tank or retort, admitting steam into the retort for heating packages at a predetermined processing temperature for a predetermined interval for sterilizing the packages and admitting cooling water and compressed air in the retort for cooling the packages. In such a method of sterilization it is necessary to decrease the heating up time of the sterilization process which is necessary to prevent deterioration of the foodstuff and to decrease the time necessary for one cycle of processing. A decrease in the cooling time is also desirable to increase the operating efficiency.

The condition necessary for sterilization is generally determined by taking into consideration the critical point of heating (usually at the center) of the substance being sterilized. Since in most foodstuffs the temperature distribution therein is not uniform when they are heated by steam, a large temperature difference occurs between their surfaces and centers, since the former is heated directly. For this reason, when the surface of the foodstuff is heated to the sterilizing temperature, the center thereof is not yet heated to the required sterilizing temperature whereas its surface is subjected to a relatively large heat hysteresis thus deteriorating the the quality of the foodstuff. Thus, it is also desirable to decrease the heating up time.

In so-called "retort foodstuffs" packed in plastic films and canned goods which can be sterilized in a retort at a high temperature and in a short time, it is necessary to increase the sterilizing temperature to decrease the sterilizing interval for the purpose of preventing the contents from deteriorating. An increase in the sterilizing temperature, however, increases the cooling time thereby increasing the time necessary for one cycle of the operation. Accordingly, it has been desired to decrease the heating up time and the cooling time when a high sterilizing temperature is used.

More particularly, if the same quantity of steam per unit time were admitted into the retort when the sterilizing temperature is increased, the heating up time between the admission of the steam and a point at which the temperature reaches the required sterilizing temperature would be prolonged thereby nullifying the advantage of utilizing high temperature for a short time.

The heating up time may be decreased by rapidly admitting a large quantity of steam into the retort in a short time. In the prior art method and apparatus, however, since the steam was supplied from a single boiler, it has been necessary to use a boiler having a large capacity. Moreover, since it is the recent trend to use a retort of large capacity and to connect a number of retorts in parallel with a single boiler, it is necessary to increase the capacity of the boiler. Under these circumstances, the actual sterilizing temperature is limited to about 120° C with the result that it has been necessary to use a relatively long heating up time of from 7 to 12 minutes.

Further, according to the prior art method and apparatus, cooling of the sterilized packages or cans has been accomplished by sprinkling water thereon and discharging the water collected in the retort by causing the water to overflow. When the cooling water is sprinkled from above, the steam in the retort rapidly condenses by the intimate contact with the cooling water thus causing a large drop in the internal pressure. If air is not admitted into the retort at a sufficiently high rate to prevent excessive pressure drop the packages or can will be ruptured due to a large difference in the pressure on the inside and outside thereof. To eliminate this difficulty, the control valve in a conduit for supplying the cooling water is opened only a little to limit the quantity of the cooling water. This, of course, increases the cooling time, deteriorates the contents of the packages and decreases the operating efficiency. When the cooling water is sprinkled from above as described above, as it reaches the bottom of the retort, its temperature will increase to such an extent that its cooling effect has been substantially lost, whereby the temperature distribution in the retort is not uniform, and only when the retort is filled with the cooling water and it begins to overflow, does a substantial cooling effect begin. Of course, the higher the sterilizing temperature, the longer the cooling time.

SUMMARY OF THE INVENTION

It is an object of this invention to provide an improved method and apparatus for effecting batch sterilization capable of heating up the sealed packages to a higher sterilizing temperature in a shorter time and sterilizing the packages for shorter time than in the conventional method thus avoiding deterioration of the packed substance.

Another object of this invention is to provide an improved method and apparatus for quickly cooling the sterilized packages to room temperature thus improving the operating efficiency.

Still another object of this invention is to provide an improved method and apparatus for batch sterilization capable of creating uniform temperature distribution throughout the sterilizing tank.

According to one aspect of this invention, there is provided a method of batch sterilization of the type wherein sealed packages containing substances to be sterilized are charged into a sterilizing tank, steam is admitted into the tank to heat and sterilize the sealed packages, and cooling water is admitted into the tank for cooling the sterilized packages, characterized in that steam is generated in a heat storage tank which is heated by steam supplied from a boiler, that the steam generated by the heat storage tank is admitted into the sterilizing tank for rapidly heating up the interior thereof to a predetermined sterilizing temperature, and that the admission of the steam generated by the heat storage tank into the sterilizing tank is continued for maintaining the sterilizing temperature for a predetermined time.

According to another aspect of this invention, there is provided a method of batch type sterilization of the type wherein sealed packages containing substances to be sterilized are charged into a sterilizing tank, the sealed packages being liable to be ruptured due to the pressure difference between inside and outside thereof, the packages are heated and sterilized in the tank and then cooling water and pressurized gas are admitted into the tank for cooling the sterilized packages, characterized in that the cooling water is admitted into the tank from the top and bottom thereof for a short interval and then the cooling water in the lower portion is circulated through the upper portion of the tank thus cooling the sterilized packages.

According to a further aspect of this invention, there is provided apparatus for batch type sterilization of the type comprising a sterilizing tank for accommodating sealed packages containing food material to be sterilized, means for admitting steam into the tank to heat and sterilize the packages and means for admitting cooling water into the sterilizing tank for cooling the sterilized packages, characterized in that there are provided a heat storage tank which is heated by steam from a boiler for generating steam, and means for admitting the steam generated by the heat storage tank into the sterilizing tank.

In this manner, as the cooling water is admitted into the upper and lower portions of the sterilizing tank and since the cooling water in the lower portion is circulated through the upper portion of the sterilizing tank, it is possible to establish uniform temperature distribution in the tank thus uniformly cooling the packages in the tank. Further, when the cooling water is admitted into the sterilizing tank through the bottom thereof, condensation of the steam contained in the tank is effected only at the interface between the steam and the cooling water so that even when a large quantity of the cooling water is admitted, the pressure in the tank does not decrease rapidly thereby preventing rupture of the package due to a rapid decrease in the internal tank pressure. The quantity of the pressurized gas admitted into the sterilizing tank together with the cooling water may be small only enough to supplement the pressure drop caused by the condensation of steam at the interface so that it is not necessary to use a source of pressurized gas having a large capacity. Actually, however, substantially all steam in the tank is condensed by the cooling water supplied into the upper portion of the tank, so that admission of the cooling water into the lower portion of the tank does not cause condensation of the steam and hence a decrease in the pressure. In this manner, the cooling effect can be enhanced by the rapid admission of the cooling water.

The heat storage tank is normally charged with a definite quantity of water which is heated by steam supplied from an independent boiler, and the capacity of the tank is selected such that it generates and stores steam having a heat quantity necessary to heat up and sterilize the packages during one cycle.

The reason that hot water can not be used to heat up and sterilize the packages at a high temperature and in a short time is that when hot water is admittied into the sterilizing tank from a hot water tank, it generates steam having the same vapour pressure at the atmosphere so that it is necessary to heat as generated steam to the desired sterilizing temperature thus requiring a longer heating up time. Further, where hot water is used, it is necessary to discharge the hot water concurrently with the admission of the cooling water during the cooling step thus greatly increasing the cooling time.

By providing a suitable valve for exhausting the air in the sterilizing tank at the time of admitting steam during the heating up step, it is possible to maintain the steam in the tank at a constant vapour pressure which is efficient to decrease the heating up time. Further, by providing suitable means for preventing the decrease of the pressure in the tank at the commencement of the cooling step, it is possible to instantaneously decrease the temperature in the tank at the time of admission of the cooling water so as to decrease the cooling time.

Where the quantity of the hot water contained in the heat storage tank is adjusted, it is possible to generate steam in a quantity sufficient to meet the steam demand of the sterilizing tank. More particularly, the heat storage tank is designed to store steam during the sterilizing step in which only a small quantity of steam is supplied to the sterilizing tank and during the interval in which the sterilizing tank is opened for loading and unloading the packages but to supply a relatively large quantity of steam during the heating up time. In this manner, since the heat storage tank supplies steam intermittently, the boiler for supplying the heating steam to the heat storage tank can have a small capacity.

BRIEF DESCRIPTION OF THE DRAWING

Further objects and advantages of the invention can be more fully understood from the following detailed description taken in conjunction with the accompanying drawing in which a single figure is a diagrammatic representation of the sterilizing apparatus embodying the invention.

DESCRIPTION OF THE PREFERRED EMBODIMENT

Referring now to the accompanying drawing, a preferred embodiment of the novel sterilizing apparatus embodying the invention shown therein comprises a retort or a sterilizing tank 1, in which sealed packages or cans containing foodstuffs or the like are heated and sterilized, and a heat storage tank 2 including a discharge pipe 4 provided with a discharge valve $V_1$ controlled by a liquid level indicating and regulating meter 3 for maintaining a constant water level in the heat storage tank 2 during operation, and a steam pipe 6 connected to a main steam pipe 7 leading to a boiler, not shown. A valve $V_2$ is included in the steam pipe 6 and is controlled by a temperature indicating and regulating meter 5 for maintaining the water in the storage tank 2 at a predetermined temperature. The tank 2 is connected to a feed water pump $P_1$ via a feed water pipe 6 including a valve $SV_2$ and to a discharge pipe 10 via a normally closed steam exhaust valve $SV_1$. The retort 1 is connected to the heat storage tank 2 via a steam pipe 12 including a valve $V_3$ controlled by a temperture indicating and regulating meter 11. Further, the retort 1 is connected to the discharge pipe 10 via an exhaust valve $V_4$ and to an air compressor 17 via an air pipe 13 including a valve $V_5$. The top and bottom of the retort 1 are connected to the feed water pump $P_1$ via pipes 6a and 6b including upper and lower feed water valves $V_{6-1}$ and $V_{6-2}$, respectively. The top and bottom of the retort 1 are interconnected by a circulating pipe 14 including a three way valve $V_7$ and a circulating pump $P_2$, one passage of valve $V_7$ being connected to the discharge pipe 10. There is provided a pressure regulator 15 responsive to the pressure in the retort 1 for operating valve $V_5$. The level of the water in the feed water tank 9 is maintained at a constant level by means of a valve 16 included in a pipe leading to a water source. Although not shown in the drawing it is to be understood that feed water valves $V_{6-1}$, $V_{6-2}$ and the valve $V_7$ in the circulating pipe 14 are controlled by a timer and a water level regulators, etc.

The sterilizing apparatus described above operates as follows: Sealed packages or cans which are liable to be ruptured by the pressure difference between the inside and outside and containing foodstuff to be sterilized are charged into the retort 1. Then steam valve $V_3$ is opened to admit a large quantity of steam into the retort through pipe 12 from the heat storage tank 2. Consequently, the air in retort 1 is compressed and its pressure increases as the admission of steam is continued. Then, exhaust valve $V_4$ which is preset to open at a predetermined pressure opens to discharge air in the retort 1 whereby the temperature in the retort increases rapidly.

To carry out sterilization at a high temperature for a short interval, the steam valve $V_3$ is controlled to supply to retort 1 a quantity of steam sufficient to maintain the desired sterilizing temperature in the retort, for example, a temperature of from 130° C to 150° C. Where the sterilizing temperature is relatively low, for example about 120° C, as the temperature in the retort reaches to from 60° C to 90° C, valve $V_5$ is opened to supply compressed air into the retort from compressor 17 via air pipe 13 for increasing the internal pressure of retort 1 so as to prevent rupture of the packages or cans caused by the heat expansion of air or gas contained therein.

After elapse of a predetermined sterilizing interval, steam valve $V_3$ is closed to stop the supply of steam while at the same time feed water valve $V_{6-1}$ is partially opened to sprinkle a relatively small quantity of cooling water from above for cooling the packages or cans. At this time, valve $V_5$ is also opened to admit compressed air to increase the internal pressure in the retort for preventing a decrease in the internal pressure caused by the decrease in temperature and for preventing rupture of the packages or cans. Thus, during the initial stage of cooling, only a relatively small quantity of cooling water is admitted from above and since compressed gas is admitted rapidly, a decrease of the pressure in the retort can be prevented. Then valve $V_{6-1}$ is fully opened and feed water valve $V_{6-2}$ is also opened to admit cooling water into the retort from the top bottom thereof. Since the interior of the retort has been preliminary cooled by the water supplied through valve $V_{6-1}$ and since compressed air has been admitted into the retort, supply of a large quantity of cooling water from the top and bottom through fully opened valves $V_{6-1}$ and $V_{6-2}$ does not result in excessive decrease in the internal pressure that causes puncture of the packages. After a short interval, circulating pump $P_2$ is operated by means of a level switch or the like to supply the cooling water from the lower portion of the retort to the upper portion thereof. When the retort is completely filled with water, valve $V_{6-1}$ is closed and the circulation of the water in the retort is continued. When the packages or cans have been cooled to a temperature of from 30° C to 60° C, the three way valve $V_7$ is switched to discharge the water in the retort through discharge pipe 10 while at the same time valve $V_5$ is closed. After completion of the discharge of water from the retort 1, circulation pump $P_2$ is stopped and three way valve $V_7$ is closed. Thereafter the retort 1 is opened to take out sterilized packages or cans. Above described cycle of operation is repeated for different batches.

Although the steam pressure in the heat storage tank 2 decreases temporarily when the steam therein is transferred into retort 1 during the heating up step, it will soon be recovered by the heating action of the steam supplied from the steam pipe 7.

In the apparatus shown in the drawing, a preferred sterilizing temperature lies in a range of from 130° C to 150° C. At these sterilizing temperatures, in addition to the advantage of sterilizing at high temperatures in a short time it is also possible to eliminate the supply of pressurized air during heating which has been necessary to overcome the defect caused by the fact that even after completion of the heating up and sterilization steps, the temperature in the packages does not come up to the sterilizing temperature in the retort and hence the pressure therein is always lower than the temperature and pressure in the retort. In other words, the sterilization is effected only by steam not containing air so that the temperature distribution in the retort can be made uniform. Further, if desired, the feed water tank 9 may be omitted. It is desirable to operate automatically various valves and pumps $P_1$ and $P_2$ in a predetermined sequence. Also it is desirable that the valve $V_5$ have a response speed faster than those of valves $V_{6-1}$ and $V_{6-2}$, and that feed water valves $V_{6-1}$ and $V_{6-2}$ can control the flow quantity linearly.

As an example, a heat storage tank having a volume of 0.72m$^3$ and a retort having the same volume were used, and steam having a temperature of 170° C and at a pressure of 7.2 ± 0.1 kg cm$^2$ was supplied to the retort from the heat storage tank. The time required for heating up the packages from room temperature to respective sterilizing temperatures was as shown in the following table. The table also shows the time required for cooling the packages after sterilization. It is to be noted that the time required for filling the retort, that is the cooling down time is extremely short since it is possible to rapidly admit cooling water.

Table

| Sterilizing Temp. (° C) | Heating time (seconds) | Cooling down time (seconds) |
|---|---|---|
| 110 | 13.6 | 19.0 |
| 120 | 14.4 | 22.0 |
| 130 | 16.4 | 28.0 |
| 135 | 20.4 | 33.5 |
| 140 | 24.0 | 48.4 |
| 145 | 30.3 | 55.3 |

At a sterilizing temperature of 135° C, a sterilizing time of 10 minutes was insufficient for packages made of a packing material RP-F (a trade name of Toyo Seikan Kaisha Ltd., in Japan) each containing a foodstuff in an amount of 180g including 7.7%, by weight, of flour as in curry and stew powders. It took about 5 to 8 minutes until the packages were cooled down to 60° C, and the total time for completing one cycle was from 15 minutes and 20 seconds to 18 minutes and 20 seconds.

As a control, when steam having a temperature of 151° C and at a pressure of 4 kg/cm$^2$ was admitted into the same retort directly from a boiler, the heating up time required to elevate the temperature in the retort from room temperature to a sterilizing temperature of 135° C was 4 minutes and the sterilization was carried out at this temperature for 10 minutes. The time required for cooling the packages to a temperature of 60° C was 5 to 8 minutes. Thus, a total of 19 to 22 minutes was required for one cycle.

In the same manner, where the sterilizing temperature was 120° C, the time required for heating up from normal temperature to 120° C was 3.5 minutes, the time for sterilization was 16 minutes and the cooling time was 5 to 8 minutes, thus requiring a total of 24.5 to 27.5 minutes for one cycle. The comparison described above shows that according to this invention it is possible to greatly reduce the heating up time until the desired sterilizing temperature is reached. Further, by varying the heat storing capacity of the heat storage tank in accordance with the requirement of the retort or sterilizing tank, it is not necessary to install a boiler having an excessively large capacity, thus making it possible to sterilize packed foodstuffs at a temperature of 120° C or above which have heretofore been impossible to heat up to the sterilizing temperature within a short time as in this invention without any deterioration.

Although it is possible to cool the sterilized packages or cans by merely admitting cooling water into the top and bottom portions of the retort without circulating the water by means of pump $P_2$, it is more efficient to operate the pump as described above.

In the example described above, in order to cool the sterilized packages from 135° C to 60° C cooling water was sprinkled from above at a rate of 18 liters per 15 seconds. Cooling water was also admitted into the bottom of the retort by opening valve $V_{6-2}$ for 34 seconds to fill the retort with water. A short time after admission of the cooling water into the bottom, pump $P_2$ was operated to circulate the water at the bottom to the upper portion of the retort. The total time required for cooling was 4 minutes.

According to the prior art method, where the same retort described above was used and where a sterilizing temperature of 135° C was used, it took 1 minute for filling the retort with cooling water and 5 to 8 minutes to cool the sterilized packings from 135° C to 60° C, and the temperature difference between the upper and lower portions of the retort was much larger than in this invention.

Thus, according to this invention, it is possible to decrease the cooling time and the heating up time to make more uniform the temperature distribution in the retort thereby enabling sterilization of foodstuffs at higher temperatures and in shorter times without deterioration.

What is claimed is:

1. In a method of batch type sterilization of the type wherein sealed packages containing substances to be sterilized are charged into a sterilizing tank having upper and lower portions, steam is admitted into the sterilizing tank into direct contact with the packages to heat and sterilize the sealed packages, and cooling water and pressurized gas are admitted into the sterilizing tank for cooling the sterilized packages, the improvement which comprises the steps of generating steam in a heat storage tank by heating up a body of water therein to a predetermined temperature by steam supplied from a boiler, the amount of water being sufficient to supply the necessary quantity of steam which when heated to the predetermined temperature is sufficient for rapid heating of the sterilizing tank, admitting the steam generated by said heat storage tank into said sterilizing tank without exhausting the steam therein until the pressure within said sterilizing tank reaches a predetermined value for rapidly heating up the interior of the sterilizing tank to a sterilizing temperature of from 135° to 150° C, continuing the admission of said steam generated by said heat storage tank into said sterilizing tank for maintaining said sterilizing temperature for a predetermined time, and admitting the cooling water into said sterilizing tank from the upper and lower portions thereof and then circulating the cooling water in the lower portion through the upper portion of said sterilizing tank, thus cooling the sterilized packages.

2. The improvement according to claim 1 wherein during cooling a relatively small quantity of the cooling water is at first admitted from the upper portion of the sterilizing tank concurrently with the admission of pressurized gas so as to prevent rapid decrease in the pressure in the sterilizing tank, and then a relatively large quantity of the cooling water is rapidly admitted into the sterilizing tank from the upper portion thereof and directly into the bottom of the sterilizing tank.

3. Apparatus for batch type sterilization comprising a sterilizing tank for accommodating sealed packages containing substances to be sterilized, said sterilizing tank having upper and lower portions, means for admitting steam into said sterilizing tank into contact with the packages to heat and sterilize said packages, means for admitting cooling water into said sterilizing tank for cooling the sterilized packages, a heat storage tank which is heated by steam from a boiler for generating the steam to be admitted into said sterilizing tank at a predetermined temperature, said heat storage tank holding an amount of water sufficient to supply the necessary quantity of steam which when heated to said predetermined temperature is sufficient for rapid heating of the sterilizing tank to the sterilization temperature needed to sterilize said packages, a first valve means coupled between said heat storage tank and said sterilizing tank for admitting the steam generated by said heat storage tank into said sterilizing tank, and a second valve means provided for said sterilizing tank and discharging to the atmosphere, said second valve means being set to open when the pressure in the sterilizing tank reaches a predetermined value, whereby when the steam is firstly introduced into the sterilizing tank, the air therein is compressed until the pressure within said sterilizing tank reaches the predetermined value and only thereafter is the compressed air in the sterilizing tank released through said second valve means thus quickly heating up the tank.

4. The apparatus according to claim 3 wherein said means for admitting said cooling water comprises a third valve coupled to the upper portion of said sterilizing tank for admitting the cooling water into the upper portion of said sterilizing tank and a fourth valve coupled to the bottom part of said sterilizing tank for admitting the cooling water into the bottom of said sterilizing tank, said third valve being opened partially at first and then opened fully together with said fourth valve, and a source of compressed gas and means coupled between said source of compressed gas and said sterilizing tank for admitting the compressed gas into said sterilizing tank from said source concurrently with the operation of said third valve.

5. The apparatus according to claim 3 which further comprises a circulation pump positioned on the outside of said sterilizing tank having an intake coupled to the lower portion of said sterilizing tank and an outlet connected to the upper portion of said sterilizing tank for sprinkling the cooling water drawn from the lower portion of said sterilizing tank into the upper portion of said sterilizing tank, and pump operating means coupled to said pump for operating said pump only after compressed gas has been admitted to said sterilizing tank.

* * * * *